United States Patent [19]
Milstein et al.

[11] Patent Number: 5,447,728
[45] Date of Patent: Sep. 5, 1995

[54] DESFERRIOXAMINE ORAL DELIVERY SYSTEM

[75] Inventors: Sam J. Milstein, Larchmont; Evgueni Barantsevitch, New Rochelle, both of N.Y.

[73] Assignee: Emisphere Technologies, Inc., Hawthorne, N.Y.

[21] Appl. No.: 168,776

[22] Filed: Dec. 16, 1993

Related U.S. Application Data

[63] Continuation-in-part of Ser. No. 51,019, Apr. 22, 1993, and a continuation-in-part of Ser. No. 143,571, Oct. 26, 1993, abandoned, which is a continuation-in-part of Ser. No. 76,803, Jun. 14, 1993, which is a continuation-in-part of Ser. No. 920,346, Jul. 27, 1992, which is a continuation-in-part of Ser. No. 898,909, Jun. 15, 1992, abandoned.

[51] Int. Cl.$^6$ .............................................. A61K 9/16
[52] U.S. Cl. .................................. 424/490; 424/489; 424/491
[58] Field of Search ............ 424/455, 490, 439, 692, 424/681; 528/328; 534/16

[56] References Cited

U.S. PATENT DOCUMENTS

| | | | |
|---|---|---|---|
| Re. 24,899 | 11/1960 | Green | 260/78 |
| 2,671,451 | 3/1954 | Bolger . | |
| 2,862,918 | 12/1956 | Meyer et al. . | |
| 2,868,740 | 1/1959 | Luce . | |
| 2,971,916 | 2/1961 | Schleicher et al. . | |
| 3,016,308 | 1/1962 | Macaulay . | |
| 3,052,655 | 9/1962 | Fox et al. | 260/78 |
| 3,057,344 | 10/1962 | Abella et al. . | |
| 3,076,790 | 2/1963 | Fox et al. | 260/78 |
| 3,170,802 | 2/1965 | Fukushima . | |
| 3,190,837 | 6/1965 | Brynko et al. . | |
| 3,474,777 | 10/1969 | Figge et al. . | |
| 3,491,093 | 1/1970 | Pachter et al. | 260/247.5 |
| 3,565,559 | 2/1971 | Sato . | |
| 3,567,650 | 3/1971 | Bakan | 252/316 |
| 3,574,382 | 4/1971 | Engel et al. . | |
| 3,576,758 | 4/1971 | Emrick . | |
| 3,725,113 | 4/1973 | Chang . | |
| 3,794,561 | 2/1974 | Matsukawa et al. | 195/29 R |
| 3,795,739 | 3/1974 | Birkmayer et al. | 424/274 |
| 3,822,348 | 7/1974 | Higashi et al. | 424/95 |
| 3,849,550 | 11/1974 | Teitelbaum . | |
| 3,937,668 | 2/1976 | Zolle . | |
| 3,939,253 | 2/1976 | Bodor et al. | 424/309 |
| 3,956,172 | 5/1976 | Saeki et al. | 252/316 |
| 3,962,416 | 6/1976 | Katzen | 424/19 |
| 4,035,507 | 7/1977 | Bodor et al. | 424/311 |
| 4,048,268 | 9/1977 | Ludwig . | |
| 4,061,466 | 12/1977 | Sjoholm et al. | 23/230 B |
| 4,117,801 | 10/1978 | Dannelly et al. | 118/20 |
| 4,147,767 | 4/1979 | Yapel . | |
| 4,183,849 | 1/1980 | Hansen . | |

(List continued on next page.)

FOREIGN PATENT DOCUMENTS 1077842  8/1976  Canada .

(List continued on next page.)

OTHER PUBLICATIONS

Yusuke Amino et al., "Phenylalanine Derivatives Enhancing Intestinal Absorption of Insulin in Mice", Chem. Pharm. Bull., 36(11):4426–4434 (1988).

(List continued on next page.)

*Primary Examiner*—Thurman K. Page
*Assistant Examiner*—William E. Benston, Jr.
*Attorney, Agent, or Firm*—Darby & Darby

[57] ABSTRACT

Modified amino acids and methods for their preparation and use as oral delivery systems for pharmaceutical agents are described. The modified amino acids are preparable by reacting single amino acids or mixtures of two or more kinds of amino acids with an amino modifying agent such as benzene sulfonyl chloride, benzoyl chloride, and hippuryl chloride. The modified amino acids form encapsulating microspheres in the presence of the active agent under sphere-forming conditions. Alternatively, the modified amino acids may be used as a carrier by simply mixing the amino acids with the active agent. The modified amino acids are particularly useful in delivering peptides, e.g. insulin or calmodulin, or other agents which are sensitive to the denaturing conditions of the gastrointestinal tract.

8 Claims, 2 Drawing Sheets

U.S. PATENT DOCUMENTS

| | | | |
|---|---|---|---|
| 4,199,561 | 4/1980 | Roth et al. | 424/32 |
| 4,217,370 | 8/1980 | Rawlings et al. | |
| 4,272,506 | 6/1981 | Schwarzberg | 424/8 |
| 4,345,588 | 8/1982 | Widder et al. | |
| 4,348,384 | 9/1982 | Horikoshi et al. | |
| 4,351,337 | 9/1982 | Sidman | |
| 4,352,883 | 10/1982 | Lim | |
| 4,357,259 | 11/1982 | Senyei et al. | |
| 4,388,304 | 6/1983 | Nyeki et al. | 424/177 |
| 4,402,856 | 9/1983 | Schnoring et al. | 428/402.22 |
| 4,405,598 | 9/1983 | Brown | 424/45 |
| 4,442,090 | 4/1984 | Kakeya et al. | 424/178 |
| 4,446,138 | 5/1984 | Pack | |
| 4,450,150 | 5/1984 | Sidman | |
| 4,460,563 | 7/1984 | Calanchi | 424/35 |
| 4,462,839 | 7/1984 | McGinley et al. | 106/198 |
| 4,473,620 | 9/1984 | Wu et al. | 428/402.24 |
| 4,483,807 | 11/1984 | Asano | |
| 4,492,684 | 1/1985 | Goosen et al. | |
| 4,518,433 | 5/1985 | McGinley et al. | 106/180 |
| 4,590,265 | 5/1986 | Bogan et al. | 536/63 |
| 4,608,278 | 8/1986 | Frank | |
| 4,613,500 | 9/1986 | Suzuki et al. | 429/85 |
| 4,647,455 | 3/1987 | DeBold | 424/95 |
| 4,666,641 | 5/1987 | Fickat et al. | |
| 4,671,954 | 6/1987 | Goldberg | |
| 4,673,566 | 6/1987 | Goosen et al. | 424/19 |
| 4,703,042 | 10/1987 | Bodor | 514/56 |
| 4,745,161 | 5/1988 | Saudek et al. | |
| 4,753,804 | 6/1988 | Iaccheri et al. | |
| 4,757,007 | 7/1988 | Satoh | |
| 4,757,024 | 7/1988 | Roper | 436/507 |
| 4,766,012 | 8/1988 | Valenti | 427/213.36 |
| 4,774,320 | 9/1988 | Tagliabue et al. | 530/328 |
| 4,789,734 | 12/1988 | Pierschbacher | 530/395 |
| 4,835,312 | 5/1989 | Itoh et al. | |
| 4,844,904 | 7/1989 | Hamaguchi et al. | 424/450 |
| 4,873,087 | 10/1989 | Morishita et al. | 424/433 |
| 4,895,725 | 1/1990 | Kantor et al. | |
| 4,925,673 | 5/1990 | Steiner et al. | 424/455 |
| 4,963,364 | 10/1990 | Fox et al. | |
| 4,976,968 | 12/1990 | Steiner | |
| 4,983,402 | 1/1991 | Steiner | |
| 4,996,292 | 2/1991 | Fox et al. | 528/328 |
| 5,055,300 | 10/1991 | Gupta | |
| 5,066,487 | 11/1991 | Morelle et al. | 424/68 |
| 5,069,936 | 12/1991 | Yen | |
| 5,100,669 | 3/1992 | Hyon et al. | |
| 5,204,099 | 4/1993 | Barbier et al. | |
| 5,206,384 | 4/1993 | Shibahara et al. | |
| 5,250,236 | 10/1993 | Gasco | |
| 5,328,992 | 7/1994 | Peter et al. | 534/16 |

FOREIGN PATENT DOCUMENTS

| | | | |
|---|---|---|---|
| 0000667A1 | 2/1979 | European Pat. Off. | |
| 0105804 | 4/1984 | European Pat. Off. | |
| 0130162A2 | 1/1985 | European Pat. Off. | |
| 0170540A1 | 2/1986 | European Pat. Off. | |
| 0342054A2 | 11/1989 | European Pat. Off. | |
| 0342056A2 | 11/1989 | European Pat. Off. | |
| 0365183 | 4/1990 | European Pat. Off. | C07C 311/21 |
| 0366277 | 5/1990 | European Pat. Off. | |
| 0448057 | 9/1991 | European Pat. Off. | |
| 0452161 | 10/1991 | European Pat. Off. | |
| 0459795 | 12/1991 | European Pat. Off. | |
| 0467389 | 1/1992 | European Pat. Off. | |
| 1351358 | 3/1964 | France | |
| 1468601 | 2/1967 | France | |
| 2133926 | 12/1972 | France | |
| 2326934 | 5/1977 | France | |
| 2424169 | 12/1974 | Germany | |
| 2565102 | 12/1985 | France | |
| 3202255 | 10/1982 | Germany | |
| 3612102 | 10/1986 | Germany | |
| 71258/2 | 12/1987 | Israel | |
| 48-24246 | of 1973 | Japan | |
| 58-35111 | of 1983 | Japan | |
| 280825 | 12/1964 | Netherlands | |
| 280826 | 12/1964 | Netherlands | |
| 146698 | 11/1982 | Norway | A61K 37/26 |
| 929401 | 6/1963 | United Kingdom | |
| 1567763 | 5/1980 | United Kingdom | |
| 85/00105 | 1/1985 | WIPO | |
| 85/00110 | 1/1985 | WIPO | |
| 87/04076 | 7/1987 | WIPO | |
| 88/01213 | 2/1988 | WIPO | |

OTHER PUBLICATIONS

Watterberg et al., "Aerosolized Cromolyn Sodium Delivery to Intubated Babies", *Pediatric Research*, 23:4(2)570A, Abstr. 2209 (1988).

Bernstein, "Cromolyn Sodium", *Chest*, 87:1 Supp. 68S–73S (1985).

Damgé et al., "New Approach for Oral Administration of Insulin with Polyalkylcyanoacrylate Nanocapsules as Drug Carrier", *Diabetes*, 37, 246–251 (Feb. 1988).

Airaudo, C. B. et al. (1987) *Journal of Food Science*, vol. 52(6), pp. 1750–1752.

(List continued on next page.)

OTHER PUBLICATIONS

Andini, S. et al. (1975) *Origins of Life*, vol. 6, pp. 147–153.
Brooke, S. L. et al. (1977) *BioSystems*, vol. 9, pp. 1–22.
Chen et al. (1975) "Evidence for Hemiacetal Formation", *Biochemistry*, vol. 18, No. 5, pp. 921–925.
Davis et al. (1983) "Leucinal Inhibits . . . ", *Pharmacology Biochemistry Behavior*, vol. 19, pp. 791–794.
Dose, K. (1974) *Origins of Life*, vol. 5, pp. 239–252.
Fasman et al. (1964) *Biochemistry*, vol. 3, No. 11, pp. 1665–1674.
Fox, S. W. et al. (1976) *BioSystems*, vol. 8, pp. 40–44.
Fox, S. W. et al., *Molecular Evolution and the Orgin of Life*, Maxel Decker, New York (1977).
Fox, S. W. et al. (1968) *Biochim. Biophys. Acta*, vol. 160, pp. 246–249.
Fox, S. W. (1976) *Origins of Life*, vol. 7, pp. 49–68.
Fox, S. W. (1980) *Naturwissenschaften*, vol. 67, pp. 378–383.
Fox, S. W. et al. (1960) *Archives of Biochemistry and Biophysics*, vol. 86, pp. 281–285.
Fox, S. W. et al. (1974) *Origins of Life*, vol. 5, pp. 227–237.
Fox, S. W. (1984) *Origins of Life*, vol. 14, pp. 485–488.
Gol'dovskii, A. M. (1978) *Zhurnal Evolyutsionnoi Biokhimii i Fiziologii*, vol. 14(6), pp. 517–519.
Gurrieri, S. et al. (1973) *Thermochimica Acta*, vol. 7, pp. 231–239.
Harada, K. et al. (1979) *BioSystems*, vol. 11, pp. 47–53.
Harada et al., (1960) *Archives of Biochemistry and Biophysics*, vol. 86, pp. 274–280.
Hare (1970) *Etude Cenetique De La Polycondensation Thermique D'χ-Amino Acides*, vol. 45, pp. 330–339.
Heinrich, M. R. et al. (1969) *Archives of Biochemistry and Biophysics*, vol. 130, pp. 441–448.
Heinz, B. et al. (1981) *BioSystems*, vol. 14, pp. 33–40.
Hennon, G. et al. (1975) *Biochimie*, vol. 57, pp. 1395–1396.
Hsu, L. L. et al. (1976) *BioSystems, vol. 8, pp. 89–101.*
Hsu, L. L. et al. (1971) *Currents in Modern Biology*, vol. 4, pp. 12–25.
Ishima, Y. et al. (1981), *BioSystems*, vol. 14, pp. 243–251.
Jackson et al. (1991) "Pharmacological . . . ", *J. Pharm. & Exp. Thera.*, vol. 261, No. 1, pp. 546–552.
Jungck, J. R. et al. (1973) *Naturwissenschaften*, vol. 60, pp. 425–427.
Kokufuta, E. et al. (1984) *BioSystems*, vol. 16, pp. 175–181.
Krampitz, G. et al. (1967) *Naturwissenschaften*, pp. *516–517.*
Krampitz, G. et al. (1968) *Naturwissenschaften*, pp. 345 and 346.
Krampitz, G. et al. (1966) *Naturwissenschaften*, pp. 7 and 8.
Lacey, Jr., J. C. et al. (1979) *BioSystems*, vol. 11, pp. 1–7, 9–17.
Martinez Luque-Romero, M. et al. (1986) *BioSystems*, vol. 19, pp. 267–272.
Masinovsky, Z. et al. (1989) *BioSystems*, vol. 22, pp. 305–310.
Matsuno, K. (1982) *BioSystems*, vol. 15, pp. 1–11.
Matsuno, K. (1984) *BioSystems*, vol. 17, pp. 11–14.
Matsuno, K. (1981) *BioSystems*, vol. 14, pp. 163–170.
McAlhaney, W. W. et al. (1976) *BioSystems*, vol. 8, pp. 45–50.
Melius, P. et al. (1987) *BioSytems*, vol. 20, pp. 213–217.
Melius, P. et al. (1975) *Bioorganic Chemistry*, vol. 4, pp. 385–391.
Melius, P. (1979) *BioSystems*, vol. 11, pp. 125–132.
Miquel, J. et al. (1971) *Currents in Modern Biology*, vol. 3, pp. 299–306.
Nakashima, T. et al. (1980) *J. Mol. Evol.*, vol. 15, pp. 161–168.
Nakashima, T. et al. (1981) *BioSystems*, vol. 14, pp. 151–161.
Novak, V. J. A. (1984) *Origins of Life*, vol. 14, pp. 513–522.
Olafsson, P. G. et al. (1971) *Polymer Letters*, vol. 9, pp. 521–528.
Phillips, R. D. et al. (1974) *Int. J. Peptide Protein Res.*, vol. 6, pp. 309–319.
Przybylski, A. T. et al. (1982) *Die Naturwissenschaften*, vol. 69, pp. 561–563.
Przybylski, A. T. et al. (1984) *Applied Biochemistry and Biotechnology*, vol. 10, pp. 301–307.
Przybylski, A. T. (1985) *BioSystems*, vol. 17, pp. 281–288.
Rohlfing, D. L. (1975) *Origins of Life*, vol. 6, pp. 203–209.

(List continued on next page.)

OTHER PUBLICATIONS

Rohlfing, D. L. (1970) *Science,* vol. 169, pp. 998–1000.

Rohlfing, D. L. (1967) *Archives of Biochemistry and Biophysics,* vol. 118, pp. 468–474.

Rohlfing, D. L. et al. *Catalytic Activities of Thermal Polyanhydro-α-Amino Acids,* pp. 373–418.

Rohlfing, D. L. et al. (1976) *BioSystems,* vol. 8, pp. 139–145.

Ryan, J. W. et al. (1973) *BioSystems,* vol. 5, pp. 115–118.

Saunders, M. A. et al. (1974) *BioSystems,* vol. 6, pp. 81–92.

Snyder, W. D. et al. (1975) *BioSystems,* vol. 7, pp. 222–229.

Sokol, P. E. (1974) *Journal of the American Oil Chemists' Society,* vol. 52, pp. 101–102.

Tschager et al. (1989) *Milchwirtschaftliche Berichte,* vol. 95, pp. 79–83.

Vaughan, G. et al. (1987) *BioSystems,* vol. 20, pp. 219–223.

Vol'kenshtein, M. V. (1989) *Molekulyarnaya Biologiya,* vol. 23(1), pp. 23–37.

Waehneldt, T. V. et al. (1968) *Biochim. Biophys. Acta,* vol. 160, pp. 239–245.

Williams et al. (1991) *J. Biol. Chem.,* vol. 266, NO. 8, pp. 5182–5190.

Yuki, A. et al. (1969) *Biochemical and Biophysical Research communications,* vol. 36(4), pp. 657–663.

Zulaski et al. (1983) "New Carboxyalkyl Inhibitors of Brain Enkenphalinase", *J. Med. Chem.,* 26, pp. 60–65.

(1985) *Chemical Abstracts,* vol. No. 105(1), Abstract No. 12027p.

(1985) *Chemical Abstracts,* vol. No. 102(6), Abstract No. 50870d.

Chemical Abstract, vol. 80(5) Abst. No. 52392a.

Bergeron, Raymond J., et al. (1994) "Macromolecular Self-Assembly of Diketopiperazine Tetrapeptides", *Journal of the American Chemical Society,* vol. 116, pp. 8479–8484.

Bergeron, Raymond J., et al. (1993) "A Comparative Study of the Iron-Clearing Properties of Desferrithiocin Analogues With Desferrioxamine B in a *Cebus* Monkey Model", *Blood* vol. 81, No. 8, pp. 2166–2173.

Bergeron, Raymond J., et al. (1992) "A Comparison of the Iron-Clearing Properties of 1,2-Dimethyl-3-Hydroxypyrid-4-One, 1,2-Diethyl-3-Hydroxpyrid-4-One, and Deferoxamine", *Blood,* vol. 79, No. 7, pp. 1882–1890.

Bergeron, Raymond J., et al. (1991) "Evaluation of Desferrithiocin and Its Synthetic Analogs as Orally Effective Iron Chelators", *Journal of Medicinal Chemistry,* vol. 34, No. 7, pp. 2072–2078.

Bergeron, Raymond et al., "A Comparative Evaluation of Iron Clearance Models", *Annals New York Academy of Sciences,* pp. 378–393.

Andriuoli, G., et al. (1990), *Haemostasis* 20 (suppl. 1): 154–158.

Caramazza, I., et al. (1991), *Thrombosis Research* 62:785–789.

Guarini, S., et al (1983), *Experimentia* 41:350–352.

Guarini, S., et al. (1985), *Pharmacological Research Communications* 17(8): 685–697.

Dal Pozzo, A., et al. (1989), *Thrombosis Research* 56:119–124.

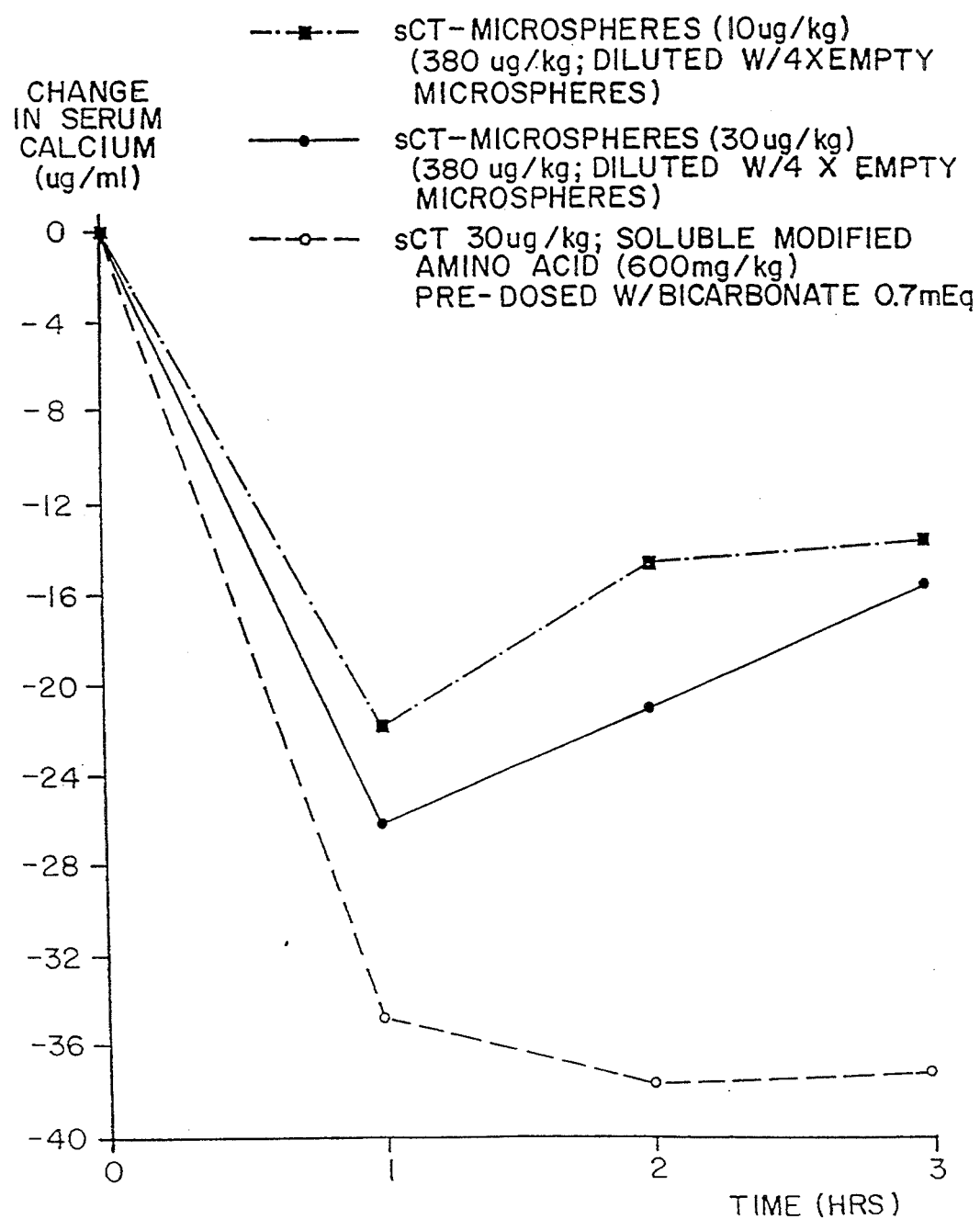

DESFERRIOXAMINE ORAL DELIVERY SYSTEM

This application is a continuation-in-part of U.S. application Ser. No. 08/051,019, filed Apr. 22, 1993, pending and of U.S. application Ser. No. 08/143,571, filed Oct. 26, 1993, abandoned, which is a continuation-in-part of U.S. application Ser. No. 08/076,803, filed Jun. 14, 1993, pending which is a continuation-in-part of U.S. application Ser. No. 07/920,346, filed Jul. 27, 1992, pending which is a continuation-in-part of U.S. application Ser. No. 07/898,909, filed Jun. 15, 1992, aband.

FIELD OF THE INVENTION

This invention related to an oral delivery system, and in particular to modified amino acids for use as a delivery system for desferrioxamine. The modified amino acids releasably encapsulate active agents and are suitable for oral administration to mammals. Methods for the preparation of such amino acids are also disclosed.

BACKGROUND OF THE INVENTION

Conventional means for delivering pharmaceutical and therapeutic agents to mammals often are severely limited by chemical or physical barriers or both, which are imposed by the body. Oral delivery of many biologically-active agents would be the route of choice if not for the presence of chemical and physicochemical barriers such as extreme pH in the gut, exposure to powerful digestive enzymes, and impermeability of gastrointestinal membranes to the active ingredient. Among the numerous pharmacological agents which are known to be unsuitable for oral administration are biologically active peptides and proteins, such as insulin. These agents are rapidly destroyed in the gut by acid hydrolysis and/or by proteolytic enzymes.

Prior methods for orally administering vulnerable pharmacological agents have relied on co-administration of adjuvants (e.g. resorcinols and non-ionic surfactants such as polyoxyethylene oleyl ether and n-hexadecyl polyethylene ether) to artificially increase the permeability of the intestinal walls; and co-administration of enzymatic inhibitors (e.g. pancreatic trypsin inhibitor, diisopropylfluorophosphate (DFF) and trasylol) to avoid enzymatic degradation. Liposomes as drug delivery systems for insulin and heparin have also been described. See, for instance, U.S. Pat. No. 4,239,754; Patel et al. (1976) *FEBS Letters* Vol. 62, page 60; and Hashimoto et al. (1979) *Endocrinol. Japan*, Vol. 26, page 337. The broader use of the aforementioned methods, however, as drug delivery systems are precluded for reasons which include: (1) the use of toxic amounts of adjuvants or inhibitors; (2) narrow range of low MW cargoes; (3) poor stability of the system and inadequate shelf life; (4) difficulty in manufacturing; and (5) the failure of the method to adequately protect the active ingredient or promote its absorption.

More recently, artificial amino acid polymers or proteinolds forming microspheres have been described for encapsulating pharmaceuticals. For example, U.S. Pat. No. 4,925,673 (the '673 patent), the disclosure of which is hereby incorporated by reference in its entirety, describes such microsphere constructs as well as methods for their preparation and use. The proteinoid microspheres of the '673 patent are useful for encapsulating a number of active agents, however the preparation methods result in a complex mixture of high molecular weight (MW) ($>1000$ daltons) and low MW ($\leq 1000$ daltons) peptidelike polymers which are difficult to separate and yield relatively small amounts of the low MW microsphere-forming fraction. Thus, there is a need in the art for a simple and inexpensive delivery system which is simple to prepare and which can encapsulate a broad range of active agents such as proteinaceous drugs.

SUMMARY OF THE INVENTION

The present invention relates to modified amino acids and modified amino acid microspheres for use as an oral delivery system for active agents and a method for preparation of such modified amino acids.

According to the invention, modified amino acids are prepared by reacting single amino acids or mixture of two or more kinds of amino acids with an acylating or sulfonating agent which reacts with free amino moieties present in the amino acids to form amides or sulfonamides, respectively. The modified amino acids are then recovered from the mixture.

The modified amino acids are non-toxic and can be orally administered to mammals as a drug delivery system by simply mixing the modified amino acids with an active agent prior to administration. Alternatively, the modified amino acid may converted into microspheres in the presence of the active agent. The microspheres, containing encapsulated active agent, are then orally administered.

DESCRIPTION OF THE DRAWINGS

FIG. 1 illustrates rat serum calcium levels after oral administration of two dosage levels of a modified amino acid microsphere preparation containing calcitonin encapsulate and soluble preparation containing modified amino acid carrier and calcitonin after pre-dosing with a sodium bicarbonate solution as described in Example 5.

DETAILED DESCRIPTION OF THE INVENTION

Figure 2A:
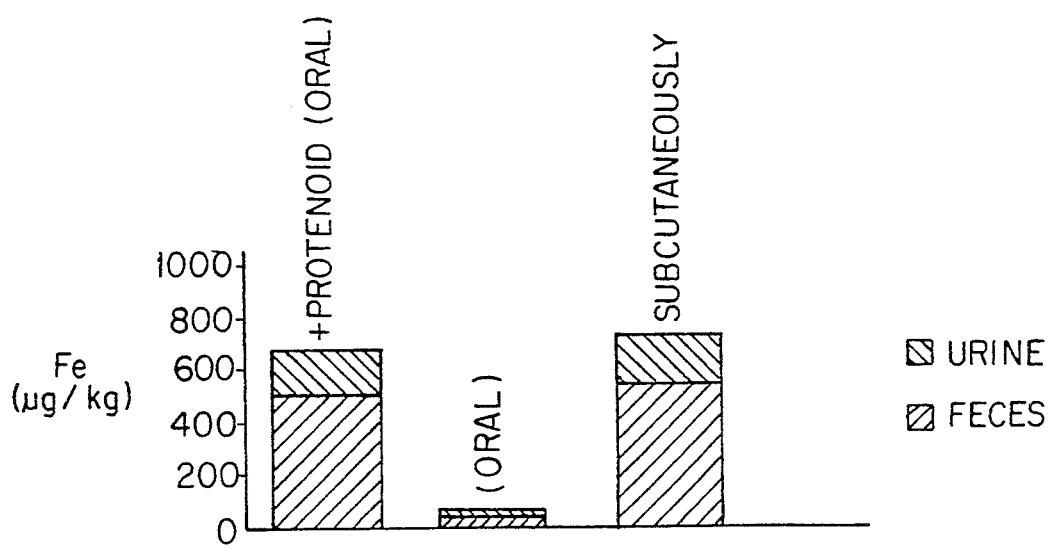
FIG. 2A, illustrates the induction of iron excretion in Cebus monkeys following oral administration of encapsulated versus unencapsulated desferrioxamine (DFO).

All patents, patent applications, and literatures cited in the specification are hereby incorporated by reference in their entirety. In the case of inconsistencies, the present disclosure, including definitions, will prevail.

The present invention arose from the discovery that amino acids, in modified form, may be used to orally deliver sensitive bioactive agents, e.g. peptide hormones such as insulin and polysaccharides such as heparin, which would not be considered orally administerable due to their sensitivity to the denaturing conditions of the gastrointestinal (GI) tract. The modified amino acids may be used as a carrier by mixing it with the active agent or may be converted into microspheres containing encapsulated bioactive agent. In contrast to the modified amino acids of the invention, unmodified free amino acids provide inadequate protective effect for labile bioactive agents against degradation in the GI tract, Other advantages provided by the present invention include the use of readily available and inexpensive starting materials and a cost-effective method for preparing and isolating modified amino acids which is simple to perform and is amenable to industrial scale-up production.

The modified amino acids of the present invention may be prepared by reacting single amino acids, mixtures of two or more kinds of amino acids, or amino acid esters with an amine modifying agent which reacts with free amino moieties present in the amino acids to form amides or sulfonamides. Amino acids and amino acid esters are readily available from a number of commercial sources such as Aldrich Chemical Co. (Milwaukee, Wis., USA); Sigma Chemical Co. (St. Louis, Mo., USA); and Fluka Chemical Corp. (Ronkonkoma, N.Y., USA).

In practicing the invention, the amino acids are dissolved in aqueous alkaline solution of a metal hydroxide, e.g., sodium or potassium hydroxide, and heated at a temperature ranging between about 5° C. and about 70° C., preferably between about 10° C. and about 40° C., for a period ranging between about 1 hour and about 4 hours, preferably about 2.5 hours. The amount of alkali employed per equivalent of $NH_2$ groups in the amino acids generally ranges between about 1.25 and about 3 mmole, preferably between about 1.5 and about 2.25 mmole per equivalent of $NH_2$. The pH of the solution generally ranges between about 8 and about 13, preferably ranging between about 10 and about 12.

Thereafter, an amino modifying agent is then added to the amino acid solution while stirring. The temperature of the mixture is maintained at a temperature generally ranging between about 5° C. and about 70° C., preferably between about 10° C. and about 40° C., for a period ranging between about 1 and about 4 hours. The amount of amino modifying agent employed in relation to the quantity of amino acids is based on the moles of total free $NH_2$ in the amino acids. In general, the amino modifying agent is employed in an amount ranging between about 0.5 and about 2.5 mole equivalents, preferably between about 0.75 and about 1.25 equivalents, per molar equivalent of total $NH_2$ groups in the amino acids.

Suitable, but non-limiting, examples of amino modifying agents useful in practicing the present invention include sulfonating agents such as benzene sulfonyl chloride and acylating agents such as benzoyl chloride, hippuryl chloride, and carbodiimide derivatives of amino acids, particularly hydrophobic amino acids such as phenylalanine, tryptophan, and tyrosine.

The reaction is quenched by adjusting the pH of the mixture with a suitable acid, e.g., concentrated hydrochloric acid, until the pH reaches between about 2 and about 3. The mixture separates on standing at room temperature to form a transparent upper layer and a white or off-white precipitate. The upper layer is discarded and modified amino acids are collected from the lower layer by filtration or decantation. The crude modified amino acids are then dissolved in water at a pH ranging between about 9 and about 13, preferably between about 11 and about 13. Insoluble materials are removed by filtration and the filtrate is dried in vacuo. The yield of modified amino acids generally ranges between about 30 and about 60%, and usually about 45%.

If desired, amino acid esters, e.g. methyl or ethyl esters of amino acids, may be used to prepare the modified amino acids of the invention. The amino acid esters, dissolved in a suitable organic solvent such as dimethylformamide or pyridine, are reacted with the amino modifying agent at a temperature ranging between about 5C and about 70C, preferably about 25C, for a period ranging between about 7 and about 24 hours. The amount of amino modifying agents used relative to the amino acid esters are the same as described above for amino acids.

Thereafter, the reaction solvent is removed under negative pressure and the ester functionality is removed by hydrolyzing the modified amino acid ester with a suitable alkaline solution, e.g. 1N sodium hydroxide, at a temperature ranging between about 50C and about 80C, preferably about 70C, for a period of time sufficient to hydrolyze off the ester group and form the modified amino acid having a free carboxyl group. The hydrolysis mixture is then cooled to room temperature and acidified, e.g. aqueous 25% hydrochloric acid solution, to a pH ranging between about 2 and about 2.5. The modified amino acid precipitates out of solution and is recovered by conventional means such as filtration or decantation.

The modified amino acids may be purified by recrystallization or by fractionation on solid column supports. Suitable recrystallization solvent systems include acetonitrile, methanol and tetrahydrofuran. Fractionation may be performed on a suitable solid column supports such as alumina, using methanol/n-propanol mixtures as the mobile phase; reverse phase column supports using trifluoroacetic acid/acetonitrile mixtures as the mobile phase; and ion exchange chromatography using water as the mobile phase. When anion exchange chromatography is performed, a subsequent 0–500 mM sodium chloride gradient is employed. The modified amino acids may also be purified by extraction with a lower alcohol such as methanol, butanol, or isopropanol to remove low molecular weight non-sphere making material.

The modified amino acids of the present invention are soluble in alkaline aqueous solution (pH $\geq 9.0$); partially soluble in ethanol, n-butanol and 1:1 (v/v) toluene/ethanol solution and insoluble in neutral water. The titratable functional groups remaining in the modified amino acids are as follows: carboxylic acid groups (COOH) generally ranging between about 1.5 and about 3.5 milliequivalents/g, preferably about 2.3 milliequivalents/g; and amino groups ($NH_2$) generally ranging between about 0.3 and about 0.9 milliequivalents/g, preferably about 0.5 milliequivalents/g.

If desired, mixtures of amino acids may be used in practicing the invention. Suitable amino acid mixtures include synthetic mixtures of two or more kinds of amino acids and readily available acid or enzyme hydrolyzed vegetable proteins. Sources of hydrolyzed liquid vegetable protein include Ajinomoto USA, Inc. (Teaneck, N.J. 07666, USA); Central Soya Co., Inc. (Fort Wayne, Ind., USA); and Champlain Industries, Inc. (Clifton, N.J., USA) and additional companies listed in "Food Engineering Master", an annual publication of Chilton Co.; Radnor, Pa. 19089, USA. Prior to modification, the hydrolyzed protein solution is dried and the amino acid mixture is extracted from dried residue with a suitable organic solvent, e.g., methanol or tetrahydrofuran, followed by evaporating the solvent extract.

A particularly preferred hydrolyzed vegetable protein for use in practicing this invention is available from Ajinomoto USA under the tradename AJI-EKI. This product is an acid hydrolyzed liquid soybean protein which is derived from defatted soybean meal and generally contains titratable carboxylic acid groups (COOH)

ranging between about 3 and about 8 milliequivalents/g preferably between about 4 and about 6 milliequivalents/g, total free amino groups (NH$_2$) ranging between about 3 and about 9 milliequivalents/g, preferably ranging between about 4 and about 6 milliequivalents/g NH$_2$. The molecular weight of the vegetable protein ranges between about 100 D and about 2000 D, preferably between about 100 and about 500 D. The modified amino acids of the present invention are stable and can stored for future use.

The modified amino acids may be used as a drug delivery carrier by simply mixing the modified amino acids with the active ingredient prior to administration. Alternatively, the modified amino acids may be used to form encapsulating microspheres containing the active agent. The modified amino acids of the invention are particularly useful for the oral administration of certain pharmacological agents, e.g., small peptide hormones, which, by themselves, pass slowly or not at all through the gastro-intestinal mucosa and/or are susceptible to chemical cleavage by acids and enzymes in the gastrointestinal tract. Non-limiting examples of such agents include human or bovine growth hormone, interferon and interleukin-II, calcitonin, atrial naturetic factor, antigens and monoclonal antibodies.

If the modified amino acids are used as a carrier for an active ingredient, an aqueous solution of modified amino acids is mixed with an aqueous solution of the active ingredient just prior to administration. The solutions may contain additives such as phosphate buffer salts, citric acid, acetic acid, gelatin and gum acacia.

A solution of the modified amino acids is prepared by mixing the amino acids in aqueous solution in an amount ranging between about 1 mg and about 2000 mg, preferably ranging between about 300 mg and about 800 mg per mL of solution. The mixture is then heated to a temperature ranging between about 20° and about 50° C., preferably about 40° C., until the modified amino acid is dissolved. The final solution contains between about 1 mg and about 2000 mg of modified amino acids per mL of solution, preferably between about 300 and about 800 mg per mL. The concentration of active agent in the final solution varies and is dependent on the required dosage for treatment.

The modified amino acids may be used to prepare microspheres for encapsulating active agents. A useful procedure is as follows: Modified amino acids are dissolved in deionized water at a concentration ranging between about 75 and about 200 mg/ml, preferably about 100 mg/ml at a temperature between about 25° C. and about 60° C., preferably about 40° C. Particulate matter remaining in the solution may be removed by conventional means such as gravity filtration over filter paper.

Thereafter, the amino acid solution, maintained at a temperature of about 40° C., is mixed 1:1 (V/V) with an aqueous acid solution (also at about 40° C.) having an acid concentration ranging between about 0.05 N and about 2 N, preferably about 1.7 N. The resulting mixture is further incubated at 40° C. for a period of time effective for microsphere formation as observed by light microscopy. In practicing this invention, the preferred order of addition is to add the amino acid solution to the aqueous acid solution.

Suitable acids include any acid which does not (a) adversely effect the modified amino acids, e.g., chemical decomposition; (b) interfere with microsphere formation; (c) interfere with microsphere encapsulation of cargo; and (d) adversely interact with the cargo. Preferred acids for use in this invention include acetic acid, citric acid, hydrochloric acid, phosphoric acid, malic acid and maleic acid.

In practicing the invention, a microsphere stabilizing additive preferably incorporated into the aqueous acid solution or into the amino acid solution, prior to the microsphere formation process. The presence of such additives promotes the stability and dispersibility of the microspheres in solution.

The additives may be employed at a concentration ranging between about 0.1 and 5% (W/V), preferably about 0.5% (W/V). Suitable, but non-limiting, examples of microsphere stabilizing additives include gum acacia, gelatin, polyethylene glycol, and polylysine.

Under these conditions, the modified amino acid molecules form hollow microspheres of less than 10 microns in diameter. If the modified amino acid microspheres are formed in the presence of a soluble material, e.g., a pharmaceutical agent in the aforementioned aqueous acid solution, this material will be encapsulated in the hollows of the microspheres and confined within the amino acid wall defined by the spherical structure. In this way, one can encapsulate pharmacologically active materials such as peptides, proteins, and polysaccharides as well as charged organic molecules, e.g., antimicrobial agents, having poor bioavailability by the oral route. The amount of pharmaceutical agent which may be encapsulated by the microsphere is dependent on a number of factors which include the concentration of agent in the encapsulating solution, as well as the affinity of the cargo for the carrier.

The modified amino acid microspheres of the invention are pharmacologically harmless and do not alter the physiological and biological properties of the active agent. Furthermore, the encapsulation process does not alter the pharmacological properties of the active agent. While any pharmacological agent can be encapsulated within the amino acid microspheres, it is particularly valuable for delivering chemical or biological agents which otherwise would be destroyed or rendered less effective by conditions encountered within the body of the mammal to which it is administered, before the microsphere reaches its target zone (i.e., the area in which the contents of the microsphere are to be released) and which are poorly absorbed in the gastrointestinal tract.

The particle size of the microsphere plays an important role in determining release of the active agent in the targeted area of the gastrointestinal tract. Microspheres having diameters between about >0.1 microns and about 10 microns, preferably between about 5.0 microns and about 0.1 microns, and encapsulating active agents are sufficiently small to effectively release the active agent at the targeted area within the gastrointestinal tract. Small microspheres can also be administered parenterally by being suspended in an appropriate carrier fluid (e.g., isotonic saline) and injected into the circulatory system or subcutaneously. The mode of administration selected will, of coursed vary, depending upon the requirement of the active agent being administered. Large amino acid microspheres (>10 microns) tend to be less effective as oral delivery systems.

The size of the microspheres formed by contacting modified amino acid with water or an aqueous solution containing active agents can be controlled by manipulating a variety of physical or chemical parameters, such as the pH, osmolarity or ionic strength of the encapsulating solution, and by the choice of acid used in the encapsulating process.

The amino acid microspheres of the invention may be orally administered alone as solids in the form of tablets, pellets, capsules, and granulates suitable for suspension in liquids such as water or edible oils. Similarly, the microspheres can be formulated into a composition containing one or more physiologically compatible carriers or excipients, and which can be administered via the oral route. These compositions may contain conventional ingredients such as gelatin, polyvinylpyrrolidone and fillers such as starch and methyl cellulose. Alternatively, small microspheres (size less than 10 μm) can be administered via the parenteral route.

The following examples are illustrative of the invention but are not intended to limit the scope of the invention.

EXAMPLE 1

Modification of Amino Acids with Benzene Sulfonylchloride

A mixture of sixteen amino acids were prepared prior to chemical modification. The constituents of the mixture are summarized in Table 1. 65 grams of the amino acid mixture (total concentration of [—$NH_2$] groups=0.61 moles) was dissolved in 760 mL of 1 N sodium hydroxide solution (0.7625 equivalents) at room temperature. After stirring for 20 minutes, benzene sulfonylchloride (78 ml, 1 equivalent) was added over a 20 minute period. The reaction mixture was then stirred for 2.5 hours, without heating. As some precipitation had occurred, additional NaOH solution (2N) was added to the solution until it reached pH 9.3. The reaction mixture stirred overnight at room temperature. Thereafter, the mixture was acidified using dilute hydrochloric acid (38%; 1:4) and a cream colored material precipitated out. The resulting precipitate was isolated by decantation and dissolved in sodium hydroxide (2N). This solution was then reduced in vacuo to give a yellow solid, which was dried on the lyophilizer (34.5 g).

TABLE 1

| Amino Acid | Amino Acid Composition | | | |
|---|---|---|---|---|
| | Weight (g) | % of Total Weight | No. of moles of each Amino Acid ($\times 10^{-2}$) | No. of Moles of -[—$NH_2$] |
| Thr | 2.47 | 3.8 | 2.07 | 2.07 |
| Ser | 2.25 | 3.46 | 2.1 | 2.1 |
| Ala | 4.61 | 7.1 | 5.17 | 5.17 |
| Val | 4.39 | 6.76 | 3.75 | 3.75 |
| Met | 0.53 | 0.82 | 0.35 | 0.35 |
| Ile | 2.47 | 3.8 | 0.36 | 0.36 |
| Leu | 3.86 | 5.94 | 2.95 | 2.95 |
| Tyr | 1.03 | 1.58 | 0.56 | 0.56 |
| Phe | 4.39 | 6.76 | 0.27 | 0.27 |
| His | 2.47 | 3.8 | 1.6 | 3.2 |
| Lys | 4.94 | 7.6 | 3.4 | 6.8 |
| Arg | 5.13 | 7.9 | 2.95 | 5.90 |
| Glutamine | 9.87 | 15.18 | 6.76 | 13.42 |
| Glutamic Acid | 9.87 | 15.18 | 6.70 | 6.70 |
| Asparagine | 3.32 | 5.11 | 2.51 | 5.02 |
| Aspartic Acid | 3.32 | 5.11 | 2.50 | 2.50 |

EXAMPLE 2

Preparation Modified Amino Acid/Salmon Calcitonin Compositions (a) Preparation of Modified Amino acid microepheres containing encapsulated Salmon Calcitonin The modified amino acid mixture, prepared in accordance with Example 1, was dissolved at 40° C. in distilled water (pH 7.2) at a concentration of 100 mg/ml. The solution was then filtered with a 0.2 micron filter and the temperature was maintained at 40° C. Salmon calcitonin (Sandoz Corp., Basil, Switzerland) was dissolved in an aqueous solution of citric acid (1.7N) and gelatin (5%) at a concentration of 150 mg/ml. This solution was then heated to 40° C. The two heated solutions were then mixed 1:1 (v/v). The resulting microsphere suspension was then filtered with glass wool and centrifuged for 50 minutes at 1000 g. The pellet was resuspended with 0.85N citric acid to a volume 5 to 7 fold less than the original volume. Salmon calcitonin concentration of the resuspended pellet was determined by HPLC. Additional microspheres were made according to the above procedure without salmon calcitonin. These "empty microspheres" were used to dilute the encapsulated salmon calcitonin microsphere preparation to a final dosing suspension for animal testing.

(b) Preparation of a Soluble Modified Amino Acid Carrier/Salmon Calcitonin System A soluble amino acid dosing preparation containing salmon calcitonin was prepared by dissolving the modified amino acid material in distilled water (pH 8) to an appropriate concentration. The solution was heated to 40° C. and then filtered with a 0.2 micron filter. Salmon calcitonin, also dissolved in distilled water, was then added to the modified amino acid solution prior to oral administration.

EXAMPLE 3

In Vivo Evaluation of Calcitonin Preparations in Rats

In vivo evaluation of modified amino acid microspheres containing encapsulated calcitonin and soluble modified amino acid carrier/calcitonin system, prepared as described in Example 2, were evaluated in rats. Rats were garaged with the oral dosing preparations and blood samples were withdrawn at various time intervals for serum calcium concentration determinations.

Nine rats are divided into three groups as follows:
1. calcitonin microspheres: 10 ug calcitonin/kg body weight by oral gavage (3 rats);
2. calcitonin microspheres: 30 ug calcitonin/kg body weight by oral gavage (3 rats); and
3. soluble (unencapsulated) modified amino acid/calcitonin system: 30 ug calcitonin/kg body weight by oral garage (3 rats). The rats were pre-dosed with 0.7 meq of aqueous sodium bicarbonate solution prior to administration of the soluble system.

Oral garage dosing of rats is performed. Calcitonin microspheres are prepared immediately prior to dosing and Group 1 rats and Group 2 rats each receive an appropriate dosage of the microsphere suspension. Group 3 rats receives the unencapsulated calcitonin/modified amino acid system. Approximately 0.5 ml of blood is withdrawn from each rat just prior to dosing ("0" time) and 1 h, 2 h and 3 h post-dosing. Serum from the blood samples are stored at −20° C.

The calcium levels of thawed serum taken from group 1-3 rats are analyzed by conventional methods. Experimental results in rats have demonstrated a significant increase in pharmacological activity (i.e., decreasing serum calcium levels) when calcitonin is orally administered either as a encapsulate in modified amino acid microspheres or a a mixture with modified amino acids as compared to basal levels. As shown in FIG. 1, soluble modified amino acid solution containing salmon calcitonin demonstrated a significant increase in pharmacological activity (i.e., decreasing serum calcium levels) when compared to basal levels after oral administration. The results show that orally administered calcitonin exerted a relatively greater biological effect when administered in its unencapsulated form with modified amino acid as carrier.

EXAMPLE 4

Modification of a Mixture of Five Amino Acids Using Benzene Sulfonyl Chloride

An 86.1 g (0.85 moles of $NH_2$) mixture of amino acids (see Table 1) was dissolved in 643 mL (1.5 equi.) of aqueous 2N sodium hydroxide solution. After stirring for 30 minutes at room temperature, benzene sulfonyl chloride (108 mL, 0.86 moles) was added portionwise into the amino acid solution over a 15 minute period. After stirring for 2.5 hours at room temperature, the pH of the reaction mixture (pH 5) was adjusted to pH 9 with additional 2N sodium hydroxide solution. The reaction mixture stirred overnight at room temperature. Thereafter, the pH of the reaction mixture was adjusted to pH 2.5 by addition of aqueous hydrochloric acid solution (4:1, $H_2O:HCl$) and a precipitate of modified amino acids formed. The upper layer was discarded and the resulting yellow precipitate was isolated by decantation, washed with water and dissolved in 2N sodium hydroxide (2N). The solution was reduced in vacuo to give a yellow solid which was lyophilized overnight. The yield of crude modified amino acid was 137.9 g.

TABLE 2

| Amino Acid | Moles of Amino Acid ($\times 10^{-2}$) | Moles of $[-NH_2] \times 10^{-2}$ |
|---|---|---|
| Valine | 7.5 | 7.5 |
| Leucine | 10.7 | 10.5 |
| Phenylalanine | 13.4 | 13.4 |
| Lysine | 21.0 | 42.0 |
| Arginine | 6.0 | 12.0 |

EXAMPLE 5

Modification of a Mixture of Five Amino Acids Using Benzoyl Chloride

An 86 g (0.85 moles of $NH_2$) mixture of amino acids (see Table 2 in Example 4) was dissolved in 637 mL (1.5 equi.) of aqueous 2N sodium hydroxide solution, After stirring for 10 minutes at room temperature, benzoyl chloride (99 mL, 0.85 moles) was added portionwise into the amino acid solution over a 10 minute period. After stirring for 2.5 hours at room temperature, the pH of the reaction mixture (pH 12) was adjusted to pH 2.5 using dilute hydrochloric acid (4:1, $H_2O:HCl$). The reaction mixture stirred overnight at room temperature. Thereafter, the pH of the reaction mixture was adjusted to pH 2.5 by addition of aqueous hydrochloric acid solution (4:1, $H_2O:HCl$) and a precipitate of modified amino acids formed. After settling for 1 hour, the resulting precipitate was isolated by decantation, washed with water and dissolved in sodium hydroxide (2N). This solution was then reduced in vacuo to give crude modified amino acids as a white solid (220.5 g).

EXAMPLE 6

Modification of L-Valine Using Benzene Sulfonyl Chloride

L-Valine (50 g, 0.43 mol) was dissolved in 376 mL (1.75 equil.) of aqueous 2N sodium hydroxide by stirring at room temperature for 10 minutes. Benzene sulfonyl chloride (48.7 mL, 0.38 mol, 1.25 equil.) was then added to the amino acid solution over a 20 minute period at room temperature. After stirring for 2 hours at room temperature, a precipitate appeared. The precipitate was dissolved by adding 200 mL of additional 2N sodium hydroxide solution, After stirring for an additional 30 minutes, dilute aqueous hydrochloric acid solution (1: 4, $H_2O:HCl$) was added until the pH of the reaction mixture reached 2.6. A precipitate of modified amino acids formed and was recovered by decantation. This material was dissolved in 2N sodium hydroxide and dried in vacuo to give a white solid. Yield of crude modified amino acids=84.6 g, 77%).

EXAMPLE 7

Modification of Phenylalanine Methyl Ester Using Hippuryl Chloride

L-Phenylalanine Methyl Ester Hydrochloride (15 g, 0.084 mole) was dissolved in dimethylformamide (DMF) (100 mL) and to this was added pyridine (30 mL). A solution of hippuryl chloride (16.6 g, 0084 moles in 100 mL DMF) was immediately added to the amino acid ester solution in two portions. The reaction mixture was stirred at room temperature overnight. The reaction mixture was then reduced in vacuo and dissolved in 1N aqueous sodium hydroxide. The solution was heated at 70° C. for 3 hours in order to hydrolyze the methyl ester to a free carboxyl group. Thereafter, the solution was acidified to pH 2.25 using dilute aqueous hydrochloric acid solution (1:3 $HCl/H_2O$). A gum-like precipitate formed and this was recovered and dissolved in 1N sodium hydroxide. The solution was reduced in vacuo to afford 18.6 g of crude modified amino acid product (Yield 18.6 g). After recrystallization from acetonitrile, pure modified phenylalanine (12 g) was recovered as a white powder. m.p. 223°-225° C.

EXAMPLE 8

Preparation and Evaluation of Desferrioxamine (DFO)-Containing Microspheres

In this Example, a study was undertaken to evaluate the relative efficacy of the iron chelator desferrioxamine B (DFO) when administered orally with modified amino acid carriers. Currently, DFO must be administered parenterally in order to treat iron overload in mammals. The currently accepted mode of treatment (subcutaneous infusion of DFO) raises problems of compliance, especially in patients who must be maintained on chelation therapy for long periods of time, and is also difficult to achieve in Third World countries with suboptimal medical facilities. Thus, there is a need for a convenient orally administrable form of DFO. Effective amounts of DFO are well known in the art and range between about 10 and about 50 mg/kg/day (or between about 0.4 to about 2.0 g/day total.)

Preparation of DFO in modified amino acid carriers was performed in the same manner as described above. DFO was obtained from Ciba-Geigy (Basel, Switzerland) under the trade name DESFERAL. DFO modified amino acid carriers were prepared with salicyloyl-Phe modified amino acid, and the final modified amino acid carrier suspension contained 125 mg/ml DFO.

The efficacy of modified amino acid carried DFO was evaluated in both the Cebus monkey iron clearance model system (Bergeron et al., Sixth Cooley's Anemia Symposium, *Ann. N.Y. Acad. Sci.* 612:378 (1991)), and in bile duct-cannulated rats (Bergeron et al., *Blood* 79:1882 (1992)).

Experimental Procedure

A. Cebus monkeys

Eight days prior to drug administration, Cebus monkeys were anesthetized with Ketamine (7-10 mg/kg intramuscularly), after which a baseline blood sample was obtained. The animals were then transferred to metabolic cages and started on a low-iron liquid diet. One day prior to administration, the animals were fasted. On day 0, the animals were anesthetized and the drug was administered at a dose of 200 mg/kg using a pill gun. An additional blood sample was obtained on day 5.

Fecal and urine samples were collected at 24-h intervals between day −3 and day +5. The volume of the urine and the wet weight of the feces were determined, after which the samples were autoclaved. The urine samples were then acidified with low-iron nitric acid. The feces samples were freeze-dried for 48h, after which their dry weight was measured; they were then refluxed for 48h with low-iron nitric acid. The iron content of the acidified urine and feces samples was then measured in triplicate on an atomic absorption spectrophotometer.

The iron clearance rates were calculated on the basis of a 1:1 DFO-iron complex. The iron output for 4 days prior to administration of the drug was averaged and subtracted from the iron clearance after administration; this value was then divided by the theoretical output to calculate the efficiency of clearance.

Oral administration of DFO in the absence of modified amino acid carriers induced little if any clearance of iron in a 48-h period following administration (FIG. 2A.) In contrast, DFO prepared with the modified amino acid carriers of the present invention prior to administration induced a rapid peak of iron secretion in both urine and feces, corresponding to a 4% clearance rate during that interval. Subcutaneously administered DFO induced a 5% clearance rate. These results demonstrate that a single dose of DFO modified amino acid carrier was substantially as effective as parenterally administered DFO in delivering a therapeutically active bioavailable dose of DFO.

B. Rats

Figure 2B:
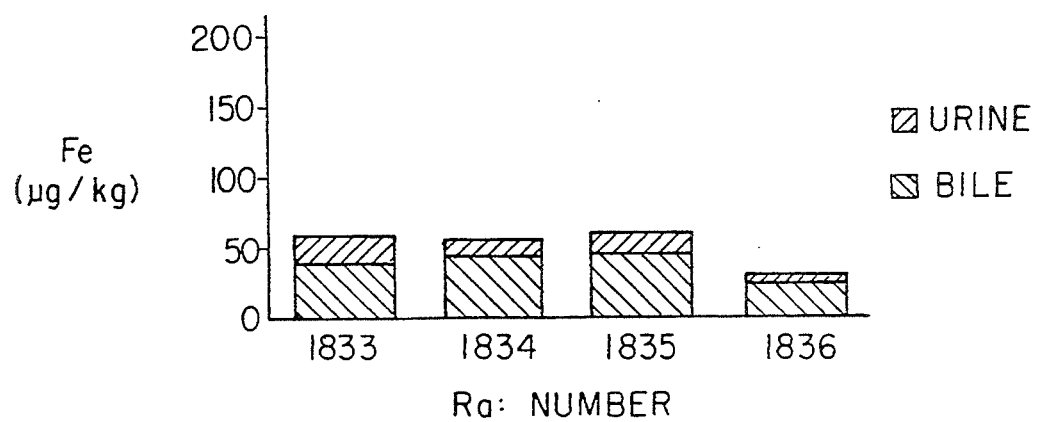
FIG. 2B shows the iron excretion in rats following oral administration of encapsulated DFO.

Male Sprague-Dawley rats were anesthetized, after which their bile ducts were cannulated, such that continuous bile samples could be collected while the animals were free to move around their cages. The rats were fasted for 24h, after which the drug was administered by garage at a dose of 45 mg/kg. Bile samples were collected at 3-h intervals, and urine samples were taken every 24 h. The iron content of the bile and urine samples were measured by atomic absorption spectrometry essentially as described in part A. FIG. 2B shows the biliary and urinary excretion of iron in rats after oral administration of DFO with modified amino acid carriers. The stimulation of iron excretion by orally administered modified acid carried DFO is equivalent to that observed when free DFO was administered via a subcutaneous route (Bergeron et al., *Blood*, ibid.).

What is claimed is:

1. A composition comprising:
   (A) desferrioxamine, and
   (B) a carrier comprising an acylated amino acid.

2. A composition as defined in claim 1, wherein said acylated amino acid comprises salicyloyl-phenylalanine.

3. A pharmaceutical composition comprising:
   (A) desferrioxamine,
   (B) a carrier comprising an acylated amino acid, and
   (C) a pharmaceutically acceptable vehicle.

4. A pharmaceutical composition as defined in claim 3, wherein said acylated amino acid comprises salicyloyl-phenylalanine.

5. A method of lowering iron concentration in a mammal, comprising orally administering to said mammal a composition as defined in claim 1.

6. A method of lowering iron concentration in a mammal, comprising orally administering to said mammal a composition as defined in claim 2.

7. A method of lowering iron concentration in a mammal, comprising orally administering to said mammal a composition as defined in claim 3.

8. A method of lowering iron concentration in a mammal, comprising orally administering to said mammal a composition as defined in claim 4.

* * * * *